(12) United States Patent
Han et al.

(10) Patent No.: US 9,884,084 B2
(45) Date of Patent: Feb. 6, 2018

(54) BONE LOSS PREVENTING AND BONE REGENERATION OR BONE FORMATION PROMOTING PHARMACEUTICAL COMPOSITION COMPRISING MURAMYL DIPEPTIDE

(71) Applicant: SNU R&DB FOUNDATION, Seoul (KR)

(72) Inventors: Seung Hyun Han, Seoul (KR); Ok-Jin Park, Seoul (KR); Cheol-Heui Yun, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 14/401,408

(22) PCT Filed: Nov. 1, 2012

(86) PCT No.: PCT/KR2012/009094
§ 371 (c)(1),
(2) Date: Nov. 14, 2014

(87) PCT Pub. No.: WO2013/172517
PCT Pub. Date: Nov. 21, 2013

(65) Prior Publication Data
US 2015/0141352 A1    May 21, 2015

(30) Foreign Application Priority Data
May 16, 2012   (KR) .................. 10-2012-0051837

(51) Int. Cl.
*A61K 38/05*    (2006.01)
*A23L 33/18*    (2016.01)
*A61K 39/00*    (2006.01)

(52) U.S. Cl.
CPC .............. *A61K 38/05* (2013.01); *A23L 33/18* (2016.08); *A23V 2002/00* (2013.01); *A61K 2039/5555* (2013.01); *A61K 2039/6062* (2013.01)

(58) Field of Classification Search
None
See application file for complete search history.

(56) References Cited

U.S. PATENT DOCUMENTS

| 4,684,625 | A | 8/1987 | Eppstein et al. |
| 5,292,506 | A | 3/1994 | Oki et al. |
| 2007/0167355 | A1 | 7/2007 | Ellithorpe et al. |

FOREIGN PATENT DOCUMENTS

| KR | 10-2010-0057055 A | 5/2010 | |
| WO | WO2008070564 A1 * | 6/2008 | |
| WO | WO2009039971 A2 * | 4/2009 | ............. A61K 38/17 |

OTHER PUBLICATIONS

Dewhirst FE. N-acetyl muramyl dipeptide stimulation of bone resorption in tissue culture. Infect Immun. Jan. 1982;35(1):133-7.*
Chedid et al. Biological activity of a new synthetic muramyl peptide adjuvant devoid of pyrogenicity. Infect Immun. Feb. 1982;35(2):417-24.*
Matsumoto et al. Stimulation of nonspecific resistance to infection induced by muramyl dipeptide analogs substituted in the gamma-carboxyl group and evaluation of N alpha-muramyl dipeptide-N epsilon-stearoyllysine. Infect Immun. Mar. 1983;39(3):1029-40.*
Raschke et al. Infection, Inflammation and osteoporosis: influence on healing and repair. European Cells and Materials vol. 16. Suppl. 4, 2008 (p. 12). ISSN 1473-2262.*

* cited by examiner

*Primary Examiner* — Satyanarayana R Gudibande
*Assistant Examiner* — Jia-Hai Lee
(74) *Attorney, Agent, or Firm* — Vorys, Sater, Seymour & Pease LLP; Min Suhn Koh (57) ABSTRACT

The present invention relates to a bone regeneration or bone formation promoting pharmaceutical composition comprising muramyl dipeptide, an analog thereof, a derivative thereof or a pharmaceutically acceptable salt thereof. In contrast to existing passive therapeutic agents which center on bone absorption suppression based on mechanisms for reducing osteoclast functionality, the composition comprising muramyl dipeptide of the present invention promotes the differentiation of osteoblasts, which are bone forming cells, and can advantageously be used in various diseases where bone formation is required as an active therapeutic agent that does not affect osteoclast.

4 Claims, 9 Drawing Sheets

Physiological saline

Muramyl-dipeptide

```
SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Forward primer for Runx2

<400> SEQUENCE: 1
ccgcacgaca accgcaccat                                              20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for Runx2

<400> SEQUENCE: 2
cgctccggcc cacaaatctc                                              20

<210> SEQ ID NO 3
<211> LENGTH: 20
<212> TYPE: DNA
<213> ORGANISM: Artificial Sequence
<220> FEATURE:
<223> OTHER INFORMATION: Reverse primer for beta-actin

<400> SEQUENCE: 3
gtggggcgcc ccaggcacca                                              20

<210> SEQ ID NO 4
<211> LENGTH: 24
<212> TYPE: DNA
<213> ORGANISM: Artificial Sequence
<220> FEATURE:
<223> OTHER INFORMATION: Reverse primer for beta-actin
```

-continued

```
<400> SEQUENCE: 4
ctccttaatc tcacgcacga tttc                                              24
```

BONE LOSS PREVENTING AND BONE REGENERATION OR BONE FORMATION PROMOTING PHARMACEUTICAL COMPOSITION COMPRISING MURAMYL DIPEPTIDE

The Sequence Listing submitted in text format (.txt) filed on Nov. 14, 2014, named "SEQLIST_OP201409002US.txt", created on Nov. 11, 2014, 1.07 KB), is incorporated herein by reference.

BACKGROUND OF INVENTION

Field of the Invention

The present disclosure relates to a new use of muramyl-dipeptide and generally relates to composition comprising muramyl-dipeptide for preventing bone loss, promoting bone regeneration or bone formation.

Description of the Related Art

Bone is a dynamic tissue that preserves skeletal size, shape, and structural integrity and kept in balance through mineral homeostasis, which is maintained through a balance between osteoblastic bone formation and osteoclastic bone resorption.

Osteoporosis is a metabolic disease which is induced with decrease in bone mass caused by aging, smoking, menopause and lack of exercise, and is widely recognized as a major public health problem and represented by fractures of the proximal femur, spine and the hipbone for which the number increases as the population ages Widely used medications for treating osteoporosis are antiresorptive type of drugs that slow bone loss by suppressing the function of osteoclast. Among them is bisphosphonates. Bisphosphonates are the most commonly prescribed drugs and proven to be effective in treating osteoporosis. However, long-term adverse effects such as osteonecrosis of the jaw have been reported. However for more complete treatment of the disease, anabolic drugs that increase the rate of bone formation are also required.

Anabolic drugs that increase the rate of bone formation is based on a parathyroid hormone. Teriparatide is currently the only osteoporosis medicine approved by the FDA that rebuilds bone. However, burden on the patients due to their high cost combined with variable efficacy depending on the patients limits their use. Therefore, there are needs for the development of new improved anabolic drugs.

Meanwhile, one of the components that are found in cell walls of the bacteria including ones found in normal flora of bacteria in human body is peptidoglycan which is also found in human bone marrow. Peptidoglycan is known to promote immunity as well as to reduce feces by promoting digestion and absorption of feed and to reduce odor by suppressing the generation of ammonia and hydrogen sulfide. However, due to its difficulty associated with the purification, peptidoglycan is usually used as a form of muramyl-dipeptide, which is a motif common to both gram negative and positive bacteria.

Korean Patent Application Publication No. 2010-7005626 discloses a use of Ac-muramyl-Ala-D-Glu-NH2 (MDP) and Ser-Phe-Leu-Leu-Arg-OH for preventing or treating cancer, infectious disease, fibrous disease, inflammatory disease and nervous disease.

U.S. Pat. No. 4,684,625 discloses a method for enhancing the anti-infective activity of muramyldipeptide derivatives.

U.S. Pat. No. 5,292,506 discloses a muramyl-dipeptide derivatives and influenza vaccine comprising the derivatives.

These documents do not disclose the use of muramyl-dipeptide for preventing bone loss, promoting bone regeneration or bone formation. Therefore there exist needs to develop a safe and effective new drug that can treat osteoporosis and related disease by increasing bone formation.

DETAILED DESCRIPTION OF THE INVENTION

Problems to be Solved

The present disclosure is to provide a therapeutic composition for treating osteoporosis, which is an anabolic drug that increases the rate of bone formation as well as amenable to a mass production with a relatively low cost.

SUMMARY OF THE INVENTION

In one aspect the present disclosure provides a pharmaceutical composition for preventing bone loss or promoting bone regeneration or bone formation, which comprises a muramyl-dipeptide, an analog thereof, a derivative thereof or a pharmaceutically acceptable salt thereof.

In one embodiment, the muramyl-dipeptide of the present composition has a structure represented by formula 1:

Formula 1 wherein $R_1$ is an acyl having 1 to 22 carbon atoms;

$R_2$ is an acyl having 1 to 22 carbon atoms;

$R_3$ is a lower alkyl having 1 to 4 carbon atoms;

$R_4$ is a hydrogen, an alkyl having 1 to 22 carbon atoms, a phenyl, or a phenyl-lower alkyl having a total of 6 to 15 carbon atoms, wherein the alkyl, phenyl and phenyl-lower alkyl may be substituted with one or more —OH, —$OR_6$, —OC(O)$R_6$, —C(O)$R_6$, —$NH_2$, —$NHR_6$ or —$N(R_6)_2$ groups, wherein $R_6$ is an alkyl having 1 to 4 carbon atoms;

$R_5$ is a hydrogen, an alkyl having 1 to 22 carbon atoms, a phenyl or a phenyl-lower alkyl having a total of 6 to 15 carbon atoms, wherein the alkyl, phenyl and phenyl-lower alkyl may be substituted with one or more —OH, —$OR_6$, —OC(O)$R_6$, —C(O)$R_6$, —$NH_2$, —$NHR_6$ or —$N(R_6)_2$ groups, wherein $R_6$ is an alkyl having 1 to 4 carbon atoms;

X is an aminoacyl selected from the group consisting of L-alanyl, L-tryptophanyl, L-valyl, L-lysyl, L-leucyl, L-ornithyl, L-isoleucyl, L-arginyl, L-α-aminobutyryl, L-histidinyl, L-seryl, L-glutamyl, L-threonyl, L-glutaminyl, L-methionyl, L-aspartyl, L-cysteinyl, L-asparaginyl, L-phenylalanyl, L-prolyl, L-tyrosyl and L-hydroxyprolyl; and Y is a D-glutamic acid or D-aspartic acid, a ($C_{1-22}$ alkyl)ester thereof, a di($C_{1-22}$ alkyl)ester thereof, an amide thereof, a ($C_{1-4}$ alkyl)amide thereof, a di($C_{1-4}$ alkyl)amide thereof, or a ($C_{1-22}$ alkyl)ester-($C_{1-4}$ alkyl)amide thereof.

In one embodiment, MDP of the present composition has a structure represented by formula 1 above, wherein $R_1$, $R_2$, $R_4$ and $R_5$ are each hydrogen, and $R_3$ is hydrogen or methyl.

In other embodiment, MDP of the present composition has a structure represented by formula 1 above, wherein X is L-alanyl, L-valyl, L-α-aminobutyryl, L-seryl or L-threonyl.

In other embodiment, MDP of the present composition has a structure represented by formula 1 above, wherein Y is D-isoglutamine, D-aspartamine or D-asparagine.

In other embodiment, MDP of the present composition is muramyl-dipeptide is selected from the group consisting of N-acetylmuramyl-L-alanyl-D-isoglutamine, N-acetylmuramyl-L-alpha-aminobutyryl-D-isoglutamine, N-acetylmuramyl-L-valyl-D-isoglutamine, and N-acetylmuramyl-L-seryl-D-isoglutamine.

It was found in the present disclosure that MDP promoted the differentiation of osteoblasts increasing the expression of bone related genes but without affecting osteoclasts, for example without increasing the number of osteoclasts and thus is very effective for the bone formation. Further the factors secreted from the osteoblasts that were increased by the present composition may further suppress the generation of osteoclasts. Thus the present composition can be advantageously used for increasing the bone formation and also preventing bone loss by osteoclasts.

Thus the present composition can be advantageously used for deformity correction, dental correction, bone fracture treatment, osteosynthesis, bone regeneration of false joints, bone formation, or bone grafting.

In other aspect, the present disclosure provides a health food supplement, a health functional food or a food additive.

In a further aspect, the present disclosure provides a method for preventing bone loss or promoting bone regeneration or bone formation in a mammal, the method comprising a step of administering to a subject an effective amount of a muramyl-dipeptide or a pharmaceutically acceptable salt thereof.

The foregoing summary is illustrative only and is not intended to be in any way limiting. Additional aspects and/or advantages of the invention will be set forth in part in the description which follows and, in part, will be obvious from the description, or may be learned by practice of the invention.

Advantageous Effects

The present composition comprising muramyl-dipeptide can be advantageously used to prevent or treat bone related disease comprising osteoporosis. In contrast to the conventional therapeutic agents which are antiresorptive types of medications that slow bone loss by suppressing the function of osteoclast, the present composition is an anabolic type of drugs that increase the rate of bone formation by promoting the differentiation of osteoblasts and expression of regulatory genes that control the bone related genes and further the factors secreted from the osteoblasts that were increased by the present composition may further suppress the osteoclasts, thus preventing the bone loss due to osteoclasts without affecting the osteoclasts.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENT

The present disclosure is based on the findings that muramyl dipeptide (MDP) was able to promote the bone formation through its activity on osteoblasts with a relatively small amount and thus preventing the bone loss caused by osteoclasts, which were confirmed through various experiments to test its activities and efficacies on osteoblasts and experimental mice using MDP as shown in FIGS. 1 to 8.

Therefore, in one aspect, the present disclosure relates to a pharmaceutical composition comprising muramyl-dipeptide, analog thereof, derivative thereof or a pharmaceutically acceptable salt thereof as an effective ingredient for preventing bone loss or promoting bone regeneration or bone formation.

The present composition comprising MDP functions as an anabolic type of drugs and is able to promote the bone formation or the bone regeneration by acting on osteoblasts. The present composition is differentiated from the conventional therapeutics which are antiresorptive type of medications that slow down bone loss by suppressing the function of osteoclast. Thus the present composition can be advantageously used for treating or preventing various bone disorders including for example, osteoporosis, bone damages caused by metastasis of cancer cells to bone, osteomalacia, rickets, osteitis fibrosa, adynamic bone disease, metabolic bone disease, osteolysis, leucopenia, bone deformity, hypercalcemia, rheumatoid arthritis, osteoarthritis, arthrosis deformans and nerve compression syndrome and the like.

Further, the present composition can also be advantageously used for preventing or treating diseases or conditions where the bone formation is suppressed. For example, the present composition is suitable for treating and/or preventing bone disorders associated with a systematic bone loss comprising such as osteogenesis imperfect, correction of malformation and orthodontics, implant accompanied by alveolar bone graft, and fracture and osteosynthesis, and for promoting local bone formation and bone regeneration for false joint and mixed bone graft.

In one embodiment, the present composition is particularly useful for treating or preventing osteoporosis.

Osteoporosis is classified into a primary and secondary osteoporosis. The primary osteoporosis is caused by a lack of calcium, vitamin D or suitable physical exercise or by smoking and also found in menopausal women and senescence men. The secondary osteoporosis, which may be developed in young people, is caused by a particular disorder or drug, in which the bone strength is decreased proportional to the drug exposure time or the severity of the disease or the drug. The disease which may cause osteoporosis includes hyperthyroidism, hyperparathyroidism, Cushing's symptom (hyperadrenocorticism), premature ovarian failure, menopause due to ovariectomy, hypogonadism, chronic liver disease (hepatocirrhosis), rheumatoid arthritis, chronic renal failure, gastrectomy and the like. The drug which may cause the secondary osteoporosis includes steroids (adrenocortical steroid), anticonvulsant (anticonvulsant), heparine and the like.

As used herein, the terms "treat," "treatment," and "treating" include alleviating, abating or ameliorating at least one symptom of a disease or condition of bone related disorder, and/or reducing severity, progression and/or duration thereof, and/or preventing additional symptoms, and includes prophylactic and/or therapeutic measures.

As used herein, the terms "prevent," "prevention," and "preventing" include the suppressing the development of the bone related disease or disorder by the administration of the present composition.

As used herein, the term "muramyl-dipeptide" is the shared structural unit of peptidoglycans from cell walls of both gram positive and gram negative bacteria. Peptidoglycan is a polymer consisting of sugars and amino acids that forms a mesh-like layer outside the plasma membrane of all bacteria. The sugar component consists of alternating residues of β-(1,4) linked N-acetylglucosamine and N-acetylmuramic acid. Attached to the N-acetylmuramic acid is a peptide chain of three to five amino acids. Muramyl dipeptide is represented by formula 1 as below and is composed of N-acetyl muramic acid linked by its lactic acid moiety to the N-terminus of dipeptide, namely, an L-alanine D-isoglutamine.

Formula 1 wherein
$R_1$ is an acyl having 1 to 22 carbon atoms;
$R_2$ is an acyl having 1 to 22 carbon atoms;
$R_3$ is a lower alkyl having 1 to 4 carbon atoms;
$R_4$ is a hydrogen, an alkyl having 1 to 22 carbon atoms, a phenyl, or a phenyl-lower alkyl having a total of 6 to 15 carbon atoms, wherein the alkyl, phenyl and phenyl-lower alkyl may be substituted with one or more —OH, —OR$_6$, —OC(O)R$_6$, —C(O)R$_6$, —NH$_2$, —NHR$_6$ or —N(R$_6$)$_2$ groups, wherein $R_6$ is an alkyl having 1 to 4 carbon atoms;
$R_5$ is a hydrogen, an alkyl having 1 to 22 carbon atoms, a phenyl or a phenyl-lower alkyl having a total of 6 to 15 carbon atoms, wherein the alkyl, phenyl and phenyl-lower alkyl may be substituted with one or more —OH, —OR$_6$, —OC(O)R$_6$, —C(O)R$_6$, —NH$_2$, —NHR$_6$ or —N(R$_6$)$_2$ groups, wherein $R_6$ is an alkyl having 1 to 4 carbon atoms;
X is an aminoacyl selected from the group consisting of L-alanyl, L-tryptophanyl, L-valyl, L-lysyl, L-leucyl, L-ornithyl, L-isoleucyl, L-arginyl, L-α-aminobutyryl, L-histidinyl, L-seryl, L-glutamyl, L-threonyl, L-glutaminyl, L-methionyl, L-aspartyl, L-cysteinyl, L-asparaginyl, L-phenylalanyl, L-prolyl, L-tyrosyl and L-hydroxyprolyl; and
Y is a D-glutamic acid or D-aspartic acid, a ($C_{1-22}$ alkyl)ester thereof, a di($C_{1-22}$ alkyl)ester thereof, an amide thereof, a ($C_{1-4}$ alkyl)amide thereof, a di($C_{1-4}$ alkyl)amide thereof, or a ($C_{1-22}$ alkyl)ester-($C_{1-4}$ alkyl)amide thereof.

As used herein the term, "alkyl" refers to a straight or branched monovalent hydrocarbon chain having 1 to 22 carbon atoms.

As used herein the term, "lower alkyl" refers to a straight or branched monovalent hydrocarbon chain having 1 to 4 carbon atoms.

As used herein the term, "acyl" refers to RC(O)— wherein R is a alkyl described as above.

As used herein the term, "aryl" refers to a phenyl or phenyl lower alkyl (for example benzyl) having 6 to 15 carbon atoms.

As used herein the term, "aminoacyl" refers to alpha amino acids having carbon atoms less than 12.

As used herein the term, "substitution" is a alkyl, acyl or aryl radical substituted with at least one of —OH, —OR$_4$, —OC(O)R$_6$, —C(O)R$_6$, —NH$_2$, —NHR$_6$, or —N(R$_6$)$_2$, in which $R_6$ is a lower alkyl described as above.

In one particular embodiment, $R_1$, $R_2$, $R_4$ and $R_5$ are each represented by a hydrogen, and $R_3$ is represented by a hydrogen or a methyl, X is L-alanyl, L-valyl, L-α-aminobutyryl, L-seryl or L-threonyl, Y is D-isoglutamine, D-aspartamine or D-asparagine.

In more particular embodiment, the present muramyl peptide includes but is not limited to N-acetylmuramyl-L-alanyl-D-isoglutamine, N-acetylmuramyl-L-alpha-aminobutyryl-D-isoglutamine, N-acetylmuramyl-L-valyl-D-isoglutamine, and N-acetylmuramyl-L-seryl-D-isoglutamine, N-acetylmuramyl-L-alanlyl-D-isoglutaminyl-N-stearoyl-L-lysine (MDP-L18), N-acetylglucosamyl-N-acetylmuramyl-dipeptide (GMDP) or Stearoyl-MDP derivatives.

Further MDP derivatives of the present disclosure include ones that are known in the art or can be prepared using the conventional methods known in the art, for example, EP 4,512, 2,677, JP 54/063016, 54/073729, 55/0192236, and U.S. Pat. Nos. 4,082,735, and 4,082,736. For example, the derivatives include but are not limited to, N-acetylmuramyl-L-alanine-D-isoglutamine-lysine, 6-O-stearoyl-N-acetylmuramyl-L-alanine-D-isoglutamine, acetylglucosamine-N-acetylmuramyl-L-alanine-D-isoglutamine, or acetylglucosamine-N-acetylmuramyl-L-alanine-D-isoglutamine-lysine and the like.

Also MDP which is included in the present composition may be synthesized by methods for example disclosed in J. M. Stewart and J. D. Young. Solid Phase Peptide Synthesis, 2nd ed., Pierce Chemical Co., Rockford, Ill. (1984); J. Meienhofer, Hormonal Proteins and Peptides, Vol. 2, Academic, New York, (1973) for the solid phase synthesis; and disclosed in E. Schroder amp; K. Lubke, The Peptides, Vol. 1, Academic Press, New York, (1965) for the liquid phase synthesis. Also Messer and Sinay, Biochem. Biophys. Res. Comm., 66, 1316 (1975) may be referred.

MDP included in the present disclosure has a structure that is simple to synthesize, or may be prepared from peptidoglycan which are extracted from cell walls of bacteria and treated with suitable enzymes followed by isolation and purification. Bacteria which may be useful for the production of MDP includes *Escherichia coli* and *lactobacillus*. *Lactobacillus* is particularly useful because it is a beneficial bacterium proven to be safe for human beings.

Pharmaceutical Compositions

The present muramyl dipeptide is useful for treating or preventing various bone disorders found in mammals which are associated with decreased bone mass. Particularly, the present composition is useful for treating or preventing osteoporosis.

In one aspect, the present disclosure relates to the use of muramyl dipeptide as an active ingredient for preparing compositions, particularly pharmaceutical compositions for bone regeneration or bone formation.

The present pharmaceutical composition comprises at least one pharmaceutically accepted carrier, excipients, binders, disintegrants, glidents, diluents, lubricants, colorants, sweetings, flavors, and/or antiseptics in addition to muramyl dipeptide as an active ingredient. The present pharmaceutical composition may be prepared using the conventional methods known in the art using the conventional solid or liquid types of carriers, excipients or diluents as described above.

The present composition comprising muramyl-dipeptide is suitable for administration by parenteral (for example, intravenous, subcutaneous, intramuscular administration), non-parenteral or inhaling route. Dosage forms include but are not limited to, for example, pills, tablets, film coated tablets, capsules, liposomes, micro- and nano-preparations, and powders and the like.

The present muramyl-dipeptide can also be used as a pharmaceutically acceptable salt thereof, which includes acid addition salts, alkali salts, or alkali earth metallic salts. For example, salts of Na, K, Li, Mg or Ca may be used Pharmaceutically acceptable salts of the present MDP have the biological activity desired for the parent MDP without toxicity. Examples of such salts include (a) such as acid addition salts formed from inorganic acids such as HCl, Hydrobromic acid, Sulfuric acid, Phosphoric acid, or Nitric acid and the like; and salts formed from organic acids such as acetic acid, oxalic acid, tartar acid, succinic acid, maleic acid, fumaric acid, gluconic acid, citric acid, maleic acid, ascorbic acid, benzoic acid, tannin acid, pamoic acid, alginic acid, polyglutamic acid, naphthalenesulfonic acid, naphthalene, disulfonic acid, polygalacturonic acid and the like; (b) base addition salts formed from metallic polycation such as Calcium, Bismuth, Barium, Magnesium, Aluminum, Copper, Cobalt, Nickel, or Cadmium and the like; or base addition salts formed from organic cation such as N,N'-dibenzylethylenediamine or ethylenediamine; or (c) the combination of (a) and (b) such as zinc tannin salt.

The present composition may comprise about 5 to 95% by weight of MDP.

Examples of the pharmaceutically acceptable carriers, excipients or diluents include lactose, starch, sucrose, cellulose, magnesium stearate, calcium secondary phosphate, calcium sulfate, talc, mannitol and ethyl alcohol and the like. Also included in the present composition are binders, lubricants, disintegrants, cyroprotectants, lyoprotectants and sweetening agents, flavors and antiseptics if needed.

Binders refer to an agent that works as an adhesive and makes the powders bind or adhere to each other agglomerating them thus forming granules. Suitable binders include, but are not limited to, for example, sugars such as sucrose, starches derived from wheat, corn, rice or potato; natural gum, such as acacia, gelatin and tragacanth; derivatives from seaweed such as alginic acid, sodium alginate and calcium ammonium alginate; cellulose based materials such as methylcellulose and sodium carboxymethylcellulose and hydroxypropylmethyl-cellulose; polyvinyl pyrrolidone; and inorganic materials, such as magnesium aluminosilicate. Binders may be comprised in the present composition in an amount ranging from about 1% to about 30% by weight, particularly about 2% to about 20% by weight, more particularly about 3% to about 10% by weight, most particularly about 3% to about 6% by weight.

Diluents are materials that generally constitutes majority of formulations or compositions. Suitable diluents include, but are not limited to, for example, sugars, such as lactose, sucrose, mannitol and sorbitol; starches derived from wheat, corn, rice or potato, and cellulose, such as microcrystalline cellulose and the like. Diluents may be comprised in the present composition in an amount ranging from about 5% to about 95% by weight, particularly about 25% to about 75% by weight, more particularly about 30% to about 60% by weight, most particularly about 40% to about 50% by weight.

Disintegrating agents are materials that comprised in the formulation to promote the integration and thus release the effective ingredients in the composition. Suitable disintegrating agents include, but are not limited to, for example, starch, "soluble in cold water" modified starch, such as sodium carboxymethyl starch; natural or synthetic gums, such as locust bean, karaya, guar, tragacanth and agar, cellulose derivatives, such as methylcellulose and sodium carboxymethylcellulose, microcrystalline cellulose and cross-linked microcrystalline cellulose, such as croscarmellose sodium, alginate, such as alginic acid and sodium alginate, clay, such as bentonite and effervescent mixture and the like. Disintegrating agents may be comprised in the present composition in an amount ranging from about 1% to about 40% by weight, particularly about 2% to about 30% by weight, more particularly about 3% to about 20% by weight, most particularly about 5% to about 10% by weight.

Lubricants are materials that are used when making dosage forms such as tablets or granules to facilitate the release of such dosage forms from mouldings or dies. Lubricants are usually added just before the compression step of a process because they need to be present on and between the surface of dosage forms and press machine. Suitable lubricants include, but are not limited to, for example, metallic stearate, such as magnesium stearate, calcium stearate or potassium stearate; stearic acid; high melting point wax; and water soluble lubricant, such as sodium chloride, sodium benzoate, sodium acetate, sodium oleate, polyethylene glycol and the like. Lubricants may be comprised in the present composition in an amount ranging from about 0.05% to about 15% by weight, particularly about 0.2% to about 5% by weight, more particularly about 0.3% to about 3% by weight, most particularly about 0.3% to about 1.5% by weight.

Glidents are materials that are used to prevent caking and to increase flowability of the granules. Suitable glidents include, but are not limited to, for example, silicon dioxide and talc. Glidents may be comprised in the present composition in an amount ranging from about 0.01% to about 10% by weight, particularly about 0.1% to about 7% by weight, more particularly about 0.2% to about 5% by weight, most particularly about 0.5% to about 2% by weight.

Coloring agents are excipients that are used to color the formulations or compositions. Suitable coloring agents include, but are not limited to, for example, food grade dyes and suitable adsorbent, such as clay or aluminum oxide. The coloring agents may be comprised in the present composition in an amount ranging from about 0.01% to about 10% by weight, particularly about 0.05% to about 6% by weight, more particularly about 0.1% to about 4% by weight, most particularly about 0.1% to about 1% by weight.

The present composition may be formulated for a sustained and controlled release of at least one of the ingredients or active ingredients. Suitable sustained release formulation include a controlled release polymer matrix formulated as a tablet or a capsule comprising porous polymer matrix capsuled or impregnated with an active ingredient or a layered tablet comprising layers regulating the rate of disintegration.

The liquid formulation of the present composition may comprise a solution, a suspension and an emulsion. The liquid formulation may comprise a solution for nasal administration or a buffering agent.

Buffering agents are added to a solution to regulate pH of the solution and to maintain it within certain ranges when acids or alkali is added to the solution or the solution is diluted with a solvent. Buffering agents with effective pH range of 2.7 to 8.5, more particularly pH ranges of 3.8 to 7.7 are preferred. Examples of such buffering agents which are suitable for administration to the patients include but are not limited to, acetate, carbonate, citrate, fumarate, glutamate, lactate, phosphate, phthalate and succinate.

Further, for the preparation of the formulation and administration of the present composition, the latest edition of "Remington's Pharmaceutical Sciences" [Mack Publishing Co., Easton Pa.] may be referred.

Health Functional Food

In other aspect, the present disclosure relates to a use of the present MDP for foods, such as functional foods, health functional foods, supplemental health products, or food additives.

As used herein the term "foods" refer to a natural or processed products containing at least one nutrients, particularly which are processed enough to be ingested without further process, and which include in general terms, foods, functional foods, health functional foods, supplemental health products, food additives and drinks.

As used herein the term "functional foods" refer to a group of foods given an additional function particularly related to health promotion or disease prevention by a physical, biochemical, or biotechnological process or refer to a processed food designed to be utilized in the body to support defense mechanism, disease prevention or recovery. Particularly it includes health functional foods.

As used herein "supplemental health foods" refer to a processed food manufactured using a raw material or ingredient having a function or activity beneficial to the body. Particularly it is a processed food prepared by extraction, concentration, purification and mixing of the nutrients or ingredients contained in the food or prepared using a certain raw material with intention to provide nutrients or some health benefit.

Health functional foods comprising the present composition or MDP may be used to prevent or benefit bone related disease such as osteoporosis and may be prepared various methods known in the related art such as food science or pharmacology. The health functional foods may be formulated as tablets, capsules, soft gels, gel caps, liquids, or powders for oral administration with or without sitologically acceptable carriers, excipients or diluents and the like.

For the administration of the health function foods, oral route is preferred. Further the present health functional foods may be advantageously used for women before and after the menopause, but the subject is not limited thereto.

The present health function foods may further comprise sitologically acceptable food additives. For example, various flavoring agents or natural carbohydrates may be used and the amount to be included may be determined according to what is known in the art. Examples of carbohydrates include a monosaccharide such as glucose, and fructose; a disaccharide such as maltose and sucrose and the like; polysaccharides such as dextrin and cyclodextrin and sugar alcohols such as xylitol, sorbitol, erythritol and the like. Examples of flavoring agents include natural flavoring agents (tau Martin, stevia extract (e.g., seed video Les Bauer A, Glee Shire gonna push, etc)) and synthetic flavoring agents (saccharine, aspartame and the like).

The present health function foods may further comprise various nutrients, vitamins, minerals (electrolyte), synthetic and natural flavors, colorants, pectic acids and salts thereof, alginates and salts thereof, organic acids, protective colloidal thickenings, pH adjusting agents, stabilizers, antiseptics, glycerin, alcohols, and carbonation agents for carbonated liquid.

The components as described above may be used separately or in combinations thereof.

The present health function foods may comprises MDP as an active ingredient in a suitable amount which varies and may be selected depending on or considering age, sex, body weight of the subject to be treated for osteoporosis or a related condition or state. Particularly an amount in the range of 0.01 g to 10.0 g for an adult per day is included in the composition. However, the amount to be used or included in the foods may be various and suitably selected depending on or considering the purpose (preventing or improving). Further when the present health function foods are used for a long term basis, the amount can be adjusted accordingly.

Methods for Promoting Bone Regeneration or Bone Formation.

Also embodied in the present disclosure is a method of treating bone disorders by administering to a subject in need thereof an effective amount of the present composition comprising MDP. The bone disorders includes osteoporosis, bone damages caused by metastasis of cancer cells to bone, osteomalacia, rickets, osteitis fibrosa, adynamic bone disease, metabolic bone disease, osteolysis, leucopenia, bone deformity, hypercalcemia, rheumatoid arthritis, osteoarthritis, arthrosis deformans and nerve compression syndrome and the like. Further, the present composition can also be advantageously used for preventing or treating diseases or conditions where the bone formation is suppressed. For example, the present composition is suitable for treating and/or preventing bone disorder associated with systematic bone loss comprising such as osteogenesis imperfect, correction of malformation and orthodontics, implant accompanied by alveolar bone graft, and fracture and osteosynthesis, and for promoting local bone formation and bone regeneration for false joint and mixed bone graft.

In the present methods the composition is administered in an effective amount that is enough to "prevent" or "treating" the disease as described above so that the disease is cured, prevented, suppressed or retarded.

As used herein the term "subject" or "patient" refers to a mammal to which the present composition may be administered for a desired effect, and includes particularly a human being and non-human primates.

The present MDP is apt for a combination therapy with other therapeutic agents to treat or prevent bone disorders. Such combination therapy refers to the administration of the present composition prior to, simultaneously with or after the administration of a therapeutic agent.

The present disclosure is further explained in more detail with reference to the following examples. These examples, however, should not be interpreted as limiting the scope of the present invention in any manner.

EXAMPLES

Example 1: The Effect of MDP on the Differentiation of Osteoblasts

N-acetylmuramyl-L-Alanyl-D-Isoglutamine commercially available from Invivogen Inc. was dissolved in endotoxin free purified water to make a solution of 5 mg/ml. To assess the effect of muramyl dipeptide on the differentiation of osteoblast, osteoblast cell line MC4 cells (ATCC CRL-2593:MC3T3-E1 Subclone 4) were incubated in an ascorbic acid free-αMEM medium containing 10% fetal bovine serum, 50 unit/ml penicillin, 50 μg/ml streptomycin at 37° C. under 100% humidity and 5% $CO_2$ atmosphere. The medium was changed every 3 days.

Figure 1:
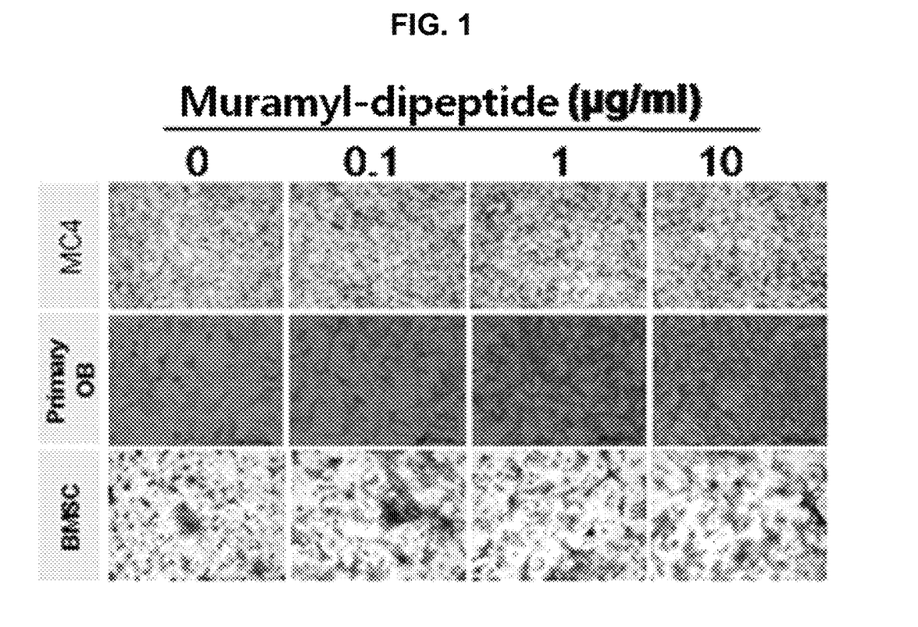
FIG. 1 is micrographs of osteoblast cell line MC4, primary osteoblasts derived from mouse calvaria and BMSCs, which were treated with various concentration of muramyl-dipeptide and then stained by detecting the alkaline phosphatase to assess the effect of the present muramyl-dipeptide on the differentiation of osteoblasts.

Then MC4 cells were seeded onto each well of a 48 well plate at the concentration of 20,000 cells/well and then after 16 hrs, each well was treated for 5 days with 400 μl of 0, 0.1, 1 and 10 μg/ml of MDP as prepared above in the differentiation medium (50 μg/ml ascorbic acid and 10 mM beta-glycerophosphate containing αMEM), during which half of the medium was changed twice with the differentiation medium. The effect on the differentiation was analyzed using alkaline phosphatase (ALP) staining. Results are shown in FIG. 1, in which the effect on the differentiation was determined by the number of cells showing red-purple color as well as the intensity of the color. FIG. 1 shows that the differentiation of MC4 was increased in a concentration dependent manner. Also when BMSC (bone marrow stem cells) derived from mouse and primary OB (osteoblast derived from mouse calvaria) were used instead of MC4 and tested under the same condition, similar results were obtained as shown in FIG. 1. Each experiment was repeated at least 3 times.

Example 2: The Effect of MDP on the Expression of Genes Involved in the Differentiation of Osteoblasts Example 2-1: The Effect of MDP on the Expression of Runx2 Gene at mRNA and Protein Level Runx2 (Runt-related transcription factor 2) is an essential gene for the differentiation of osteoblast, skeletal morphogenesis and functions as a scaffold for nucleic acids and regulatory factors involved in the expression of skeletal genes. Thus, it is known that the absence of Runx2 leads to lack of bone formation. Therefore the following experiments were performed using Runx2 as a differentiation indicator to examine the effect of MDP on the expression of Runx2 gene.

Figure 2:
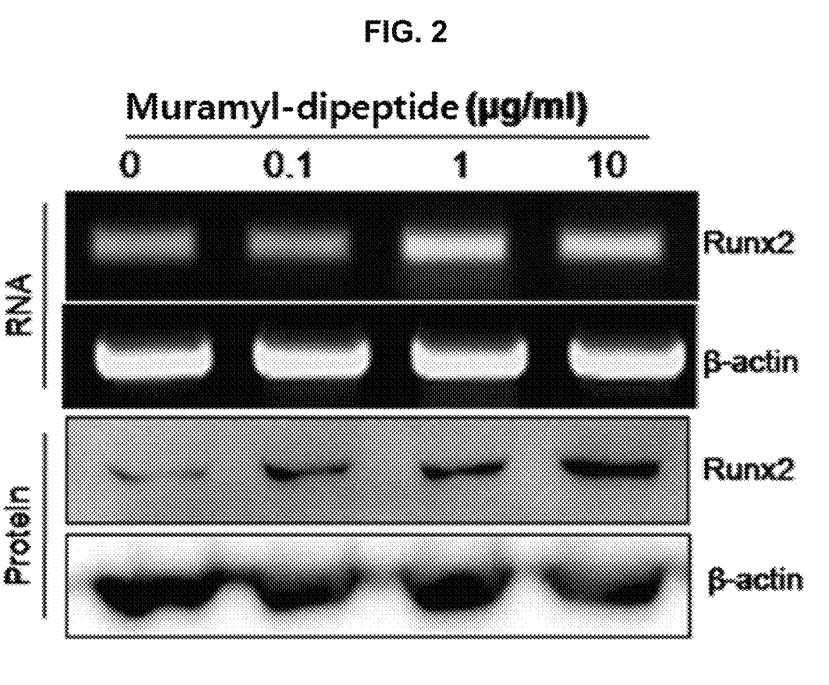
FIG. 2 is a result of RT-PCR of RNA extracted from MC4 cells treated with various concentration of muramyl-dipeptide for 6 hrs to assess the effect of the present muramyl-dipeptide on the expression of Runx2 at the mRNA level, which is essential for the differentiation of osteoblasts (upper part) and is a result of immunoblots using protein extracts from MC4 cells treated with muramyl-dipeptide for 24 hrs to assess the effect of the present muramyl-dipeptide on the expression of Runx2 at the protein level (lower part).

Firstly, MC4 cells as described in Example 1 were treated with various concentrations of MDP as indicated in FIG. 2 for 6 hrs. Then, total mRNA was extracted from the cells and incubated with random primer at 70° C. for 5 min. After that reverse transcriptase, buffer for RT and dNTPs were added to the reaction mixture and incubated at 42° C. for 1 hr to synthesize cDNA, which was then used as a template for PCR to amplify Runx2 using specific primers as described in Table 1 and using the following condition: cDNA was initially denatured at 94° C. for 5 min followed by 25 cycles at 95° C. for 40 s, 59° C. for 40 s, and 72° C. for 40 s and final extension for 5 min at 72° C. As shown in FIG. 2 (upper part) the mRNA expression of Runx2 was found to be increased after MDP treatment in a concentration dependent manner. The results were normalized relative to β-actin data.

TABLE 1

|  | Forward primer | Reverse primer |
| --- | --- | --- |
| Runx2 | CCG CAC GAC AAC CGC ACC AT | CGC TCC GGG CCA CAA ATC TC |
| β-actin | GTG GGG CGC CCC AGG CAC CA | CTC CTT AAT CTC ACG CAC GAT TTC |

Also to examine the effect at the protein level, whole cell extract was prepared from the cells treated with MDP for 24 hrs as described above, and 40 μg of extract was used for SDS-PAGE electrophoresis. Then the gel was transferred to a PVDF membrane and immunoblot was performed using an antibody specific to Runx2 (Abcam, USA). As shown in FIG. 2 (lower part), MDP increased the expression of Runx2 protein. The β-actin was used as a loading control.

Figure 3A:
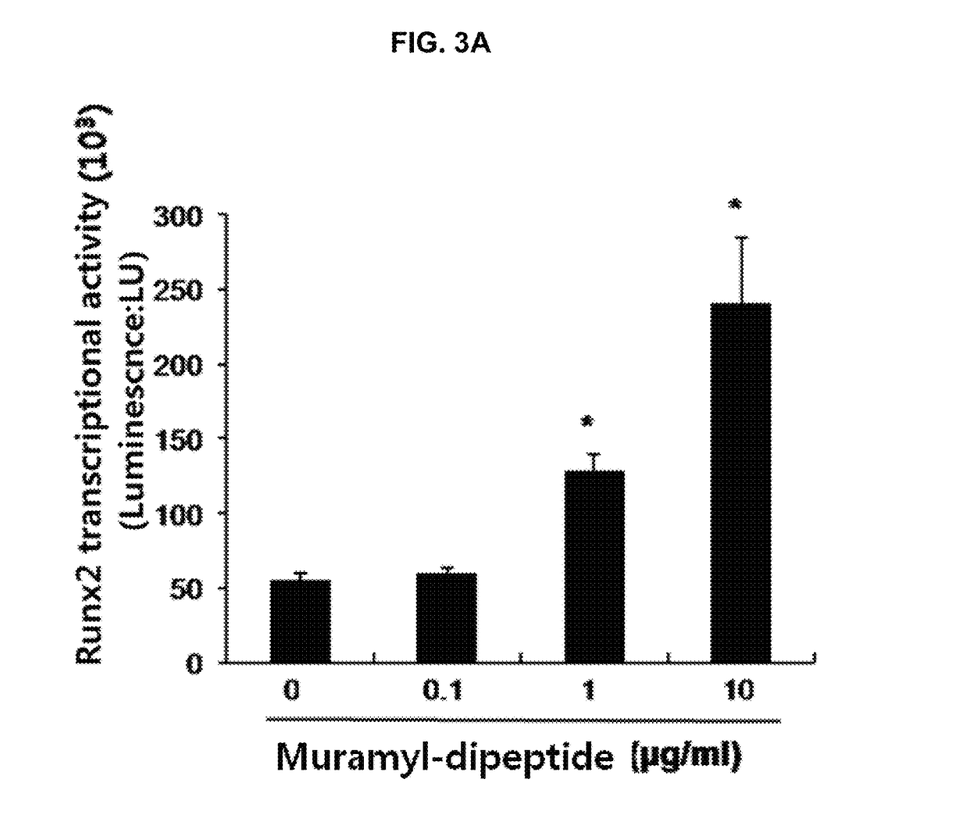
FIG. 3A is a graph showing the transcriptional activity of Runx2 in cells treated with the present muramyl-dipeptide using a reporter system which is under the control of Runx2 promoter.

Further to examine whether the increased expression of Runx2, which is a transcription factor, affects the expression of other genes regulated by Runx2, the following experiments were performed. For this, MC4 cells were seeded onto each well of a 96 well plate at the concentration of 20,000 cells/well and the cells were transfected with a plasmid 6XOSE/Luc reporter vector (Journal of Biological Chemistry. 285: 3568-3574 (2010)) which expresses luciferase gene under the control of osteocalcin using Lipofectamin® (Life technologies, Inc) according to the manufacturer's instruction. The promoter in the plasmid contains five motifs to each of which Runx2 binds. By binding of Runx2 to the motif, the expression of luciferase increases. After 16 hrs after the transfection, MDP at the concentration as indicated in FIG. 3 was added to the cells. After 24 hrs, the cells were lysed and the luciferase activity was measured using Luciferase detection kit (Promega, USA) according to the manufacturer's instruction to quantify the mRNA level of osteocalcin gene, which is affected by Runx2. As shown in FIG. 3A, muramyl dipeptide increased the expression of Runx2, which then increased the transcription of osteocalcin.

Example 2-2: The Effect of Derivative of Muramyl Dipeptide on the Transcriptional Activity of Runx2

In addition to MDP as used in Example 2-1, as a derivative thereof, M-TriLYS (MurNAc-Ala-D-isoGln-Lys, N-acetylmuramyl-L-alanine-D-isoglutamine-lysine) and 6-O-stearoyl-N-acetylmuramyl-L-alanyl-D-isoglutamine (L18-MDP) were used to examine the effect of the derivatives on the expression of Runx2 at transcription level. M-TriLYS is a muropeptide obtainable from peptidoglycans of lactobacillus or salivarius and contains in its structure muramyl dipeptide. L18-MDP is a MDP derivative containing C18 fatty acid.

Figure 3B:
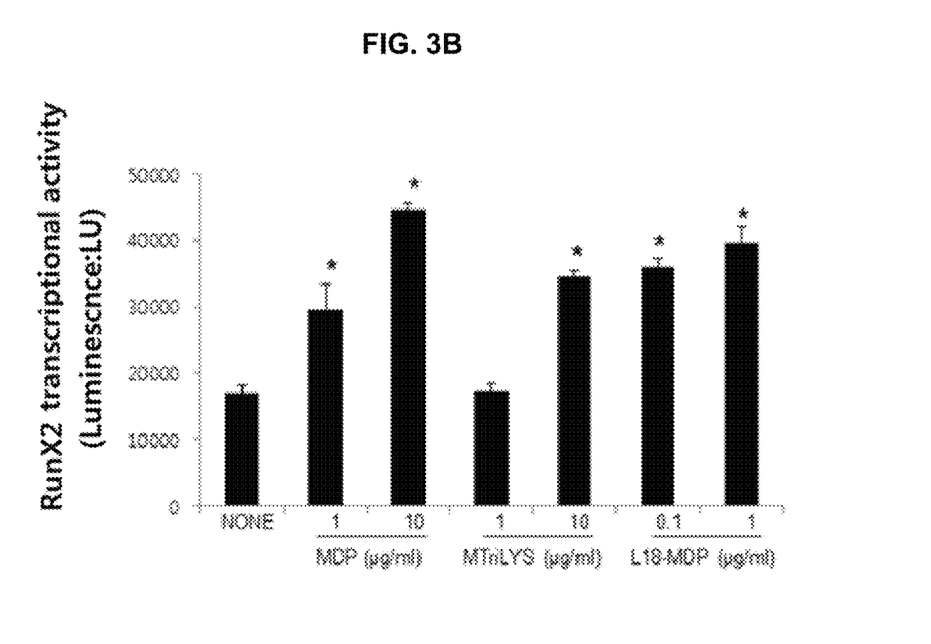
FIG. 3B is a graph showing the transcriptional activity of Runx2 in cells treated with the present muramyl-dipeptide, L18-MDP or MTriLys using a reporter system which is under the control of Runx2 promoter.

As shown in FIG. 3B, similar results were obtained using MDP, MTnLYS and L18-MDP, all of which increased the expression of Runx2 at the transcriptional level. Notably, L18-MDP showed the activity on Runx2 10 times higher than that of MDP. These results indicate that not only MDP but also its derivatives can be effective for the desired effects.

Example 3: Evaluation of Bone Formation in Mice

Example 3-1: Experimental Mice

Six-week-old WT C57BL/6 (B6) mice were purchased from Orient Company Ltd (Seoul, Korea). The animals were maintained at a controlled temperature (21±1° C.) and humidity (55±1%) with a 12/12-h light-dark cycle without any restriction of food and water. All animal experiments were performed following the protocol approved by the Institutional Animal Care and Use Committee of CRISNUH.

Example 3-2: Administration of Test Material

To each mouse, 1.25 mg/kg of MDP prepared as described in Example 1 was administered twice with a 4 day interval by intraperitoneal injection. Physiological saline was used as a control. The second injection was given 4 days after the first injection and after 3 days the mice were sacrificed and used for bone volume analysis.

Example 3-3: Determination of Bone Volume

Figure 4:
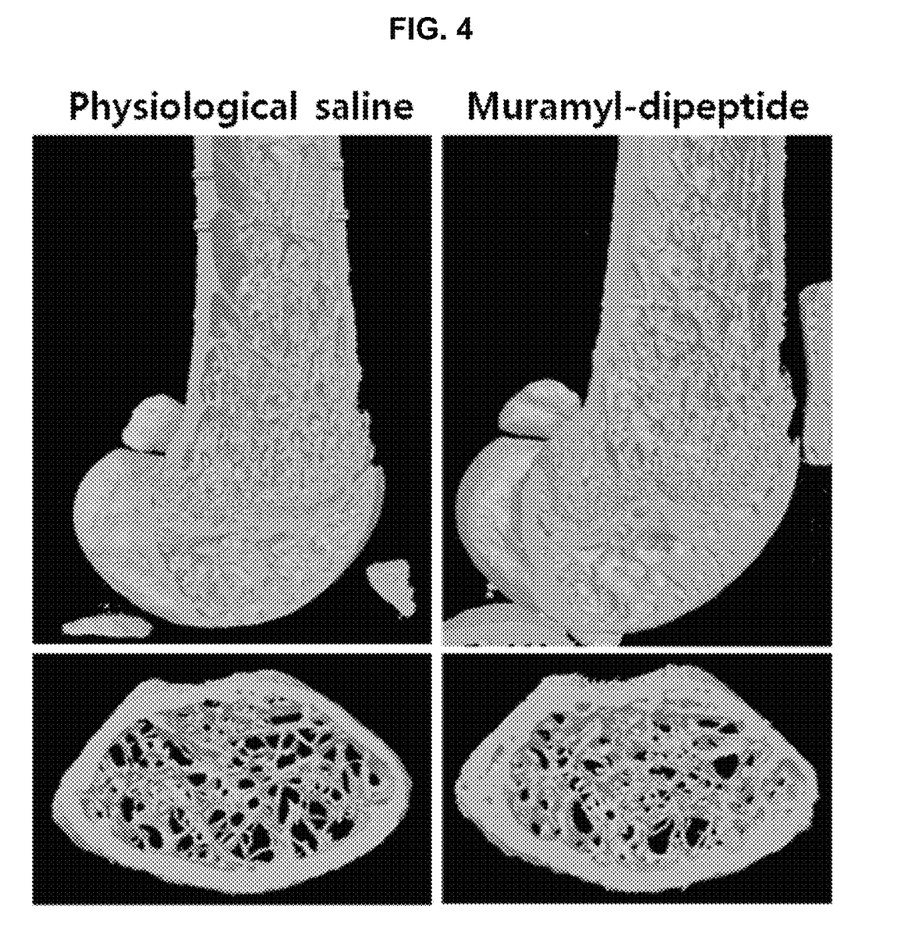
FIG. 4 is 3D images of high-resolution micro-computed tomography (microCT) of femur from mice treated with the present muramyl-dipeptide to assess changes in trabecular bone volume in which the control group was treated with physiological saline and the experimental group was treated with the present muramyl-dipeptide.
Figure 5:
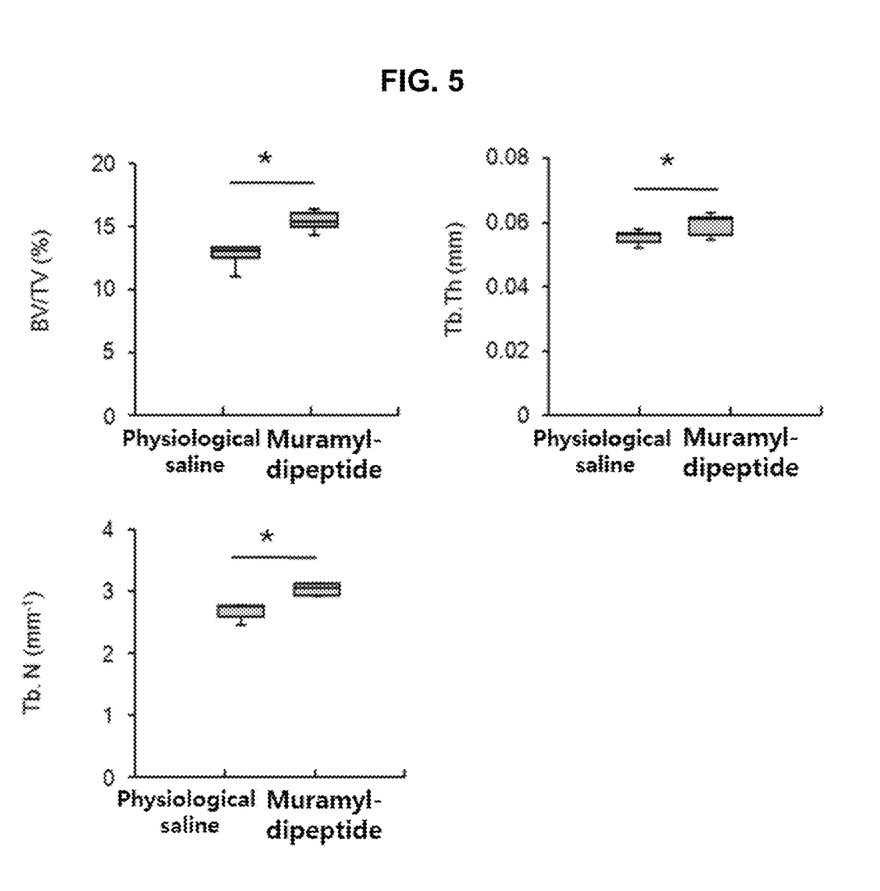
FIG. 5 is graphs showing Trabecular thickness (Tb.Th) and Trabecular number (Tb.N) in mice treated with the present muramyl-dipeptide or physiological saline as a control, in which BV/TV represents bone volume and was calculated as % of Bone volume/Tissue volume.

A right femur was removed from the sacrificed mouse and stripped of the muscle. The excised femur was then fixed in 10% of neutral formalin for one day at the least, which was then analyzed for bone volume using microCT. MicroCT data showing a 3D histological image based on the measured bone volume are shown in FIG. 4, in which the mice treated with muramyl dipeptide showed an increase in bone volume compared to the control treated with physiological saline. Also as in FIG. 5, both Trabecular thickness (Tb.Th) and Trabecular number (Tb.N) as well as Trabecular bone volume were shown to be increased statistically significantly in the mice treated with MDP compared to the control. In FIG. 5, BV/TV=Bone volume/Tissue volume=% bone volume.

Example 3-4: Histological Observation

The femur used for the analysis of bone volume in Example 3-3 was used for a histological observation. For this, the femur was demineralized in 10% EDTA for 7 days and washed with running water for 12 hrs in a tissue capsule. After that, the femur was treated with alcohol and xylene and embedded in paraffin, from which sections having a thickness of 4 μm were prepared. The sections were then placed on a slide glass and deparaffinized at 65° C. for 30 min and treated with Hematoxylin and Eosin according to the conventional method.

Figure 6:
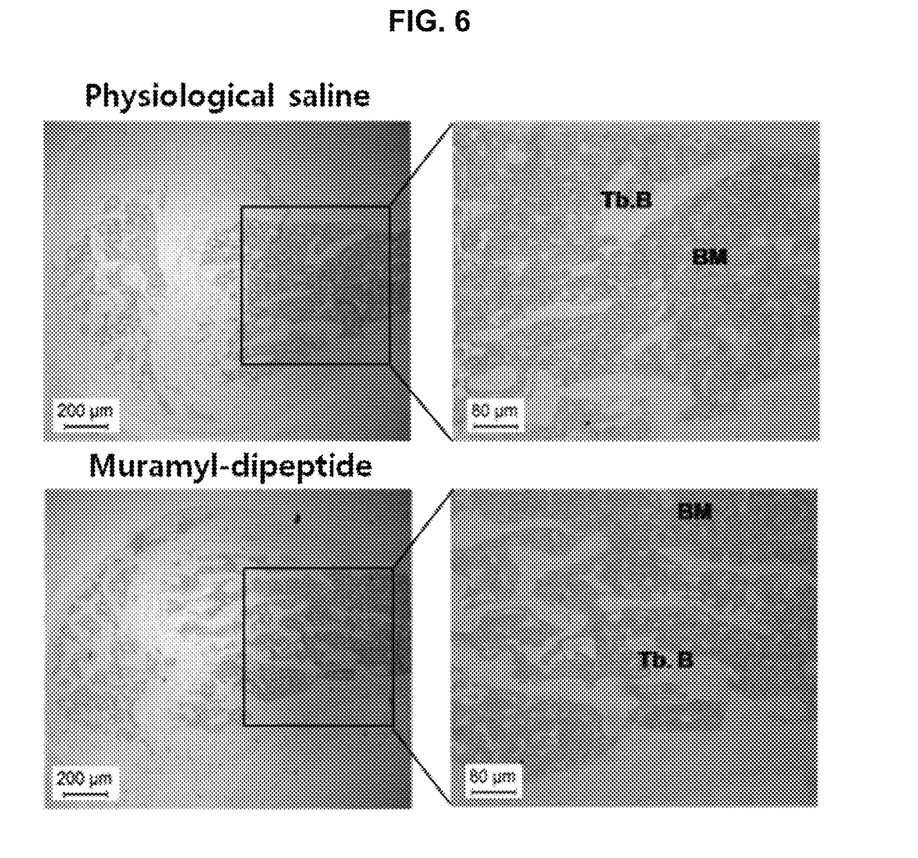
FIG. 6 is micrographs of femur of the mice stained with H&E after treated with the present muramyl-dipeptide or treated with physiological saline as a control to assess the effect of MDP on bone formation.

The slides were then examined with a light microscope to observe the bone formation. As shown in FIG. 6, more spongy bone was observed in the mice treated with MDP compared with the control treated with physiological saline. This indicates the increase in bone volume by the administration of MDP.

Example 4: The Effect of Muramyl Dipeptide on the Differentiation into Osteoclasts Bone marrow cells (BMs) were isolated from the long bones of mouse and were cultured in α-MEM supplemented with 10% FBS, 100 U/ml penicillin and 100 μg/ml streptomycin, and 2 ng/ml M-CSF for 1 day. Suspended cells were differentiated into BMMs with 20 ng/ml M-CSF for 3 days. The BMMs were incubated with 20 ng/ml M-CSF and 20 ng/ml RANKL in the presence or absence of MDP for additional 3 days. To make RANKL-primed osteoclast precursors, the BMMs were stimulated with 20 ng/ml mouse RANKL for 48 h. The BMMs were incubated with 20 ng/ml M-CSF in the presence or absence of MDP for additional 3 days.

The differentiation was determined by tartrate resistant acid phosphatase (TRAP) staining using Leukocyte acid phosphate-staining kit (Sigma-Aldrich Chemical, USA) according to the manufacturer's instruction. After the staining, TRAP-positive multinucleated cells with at least 3 nuclei were enumerated as mature osteoclasts with an inverted phase-contrast microscope and results are shown in FIG. 7.

Figure 7:
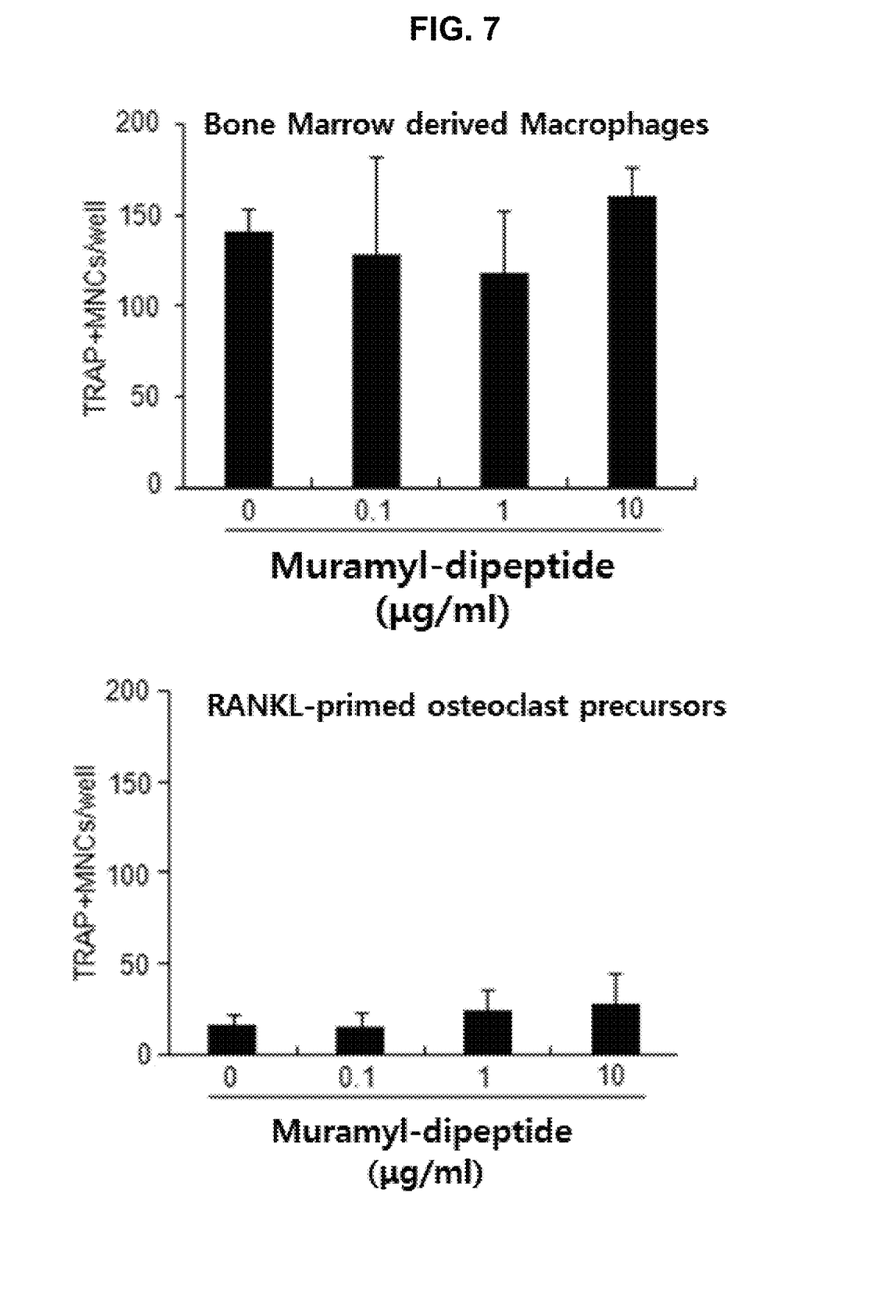
FIG. 7 is results from macrophages derived from bone marrow and RANKL-primed osteoclasts treated with various concentrations of muramyl-dipeptide to assess the effect of the muramyl-dipeptide on the differentiation of osteoclasts.

As shown in FIG. 7, it was found that muramyl dipeptide did not affect the differentiation into osteoclast from bone marrow macrophages. Also Muramyl dipeptide did not affect osteoclast differentiation from RANKL-primed osteoclast precursors which is TRAP-positive mononucleated cells (FIG. 7, Right graph). In contrast it was shown that MDP indirectly alleviated osteoclast differentiation through up-regulation of Osteoprotegerin (OPG), also known as osteoclastogenesis inhibitory factor (OCIF), and down-regulation of RANKL in the osteoblast (data not shown).

These results indicate that muramyl dipeptide do not directly but indirectly affect the differentiation of the cells into osteoclasts. Thus the present composition can be advantageously used for increasing the bone formation and also for preventing bone loss by osteoclasts.

Example 5: In Vivo Effect of Muramyl Dipeptide on the Prevention of Osteoclasia Using a Mouse Model Muramyl dipeptide was administered to a mouse by an intraperitoneal injection two times with four day interval between the administration at the concentration of 1.25 mg/kg. After 3 days of the administration, GST-RANKL recombinant protein was intraperitoneally administered at the concentration of 1 mg/kg three times with a 24 hr interval between the administrations, The bone volume was analyzed at 1 day after the last administrated with GST-RANKL. The recombinant protein was prepared using a RANKL expression vector, pGEX-GST-RANKL (J. Clin Invest. 106:1481-1488 (2000)), which was expressed in *E. coli* and the protein was purified using a sepharose gel attached with glutathione (glutathione-sepharose gels, Sigma-Aldrich). The purified protein was then treated with Detoxi-gel endotoxin removing gel (Thermo Scientific, USA) to remove endotoxin and used for the experiment. Seven days after the administration, mice were sacrificed and the bone volume was measured using a microCT. As controls, mice treated only with physiological saline, GST-RANKL or physiological saline and GST-RANKL in a consecutive order were used.

Figure 8:
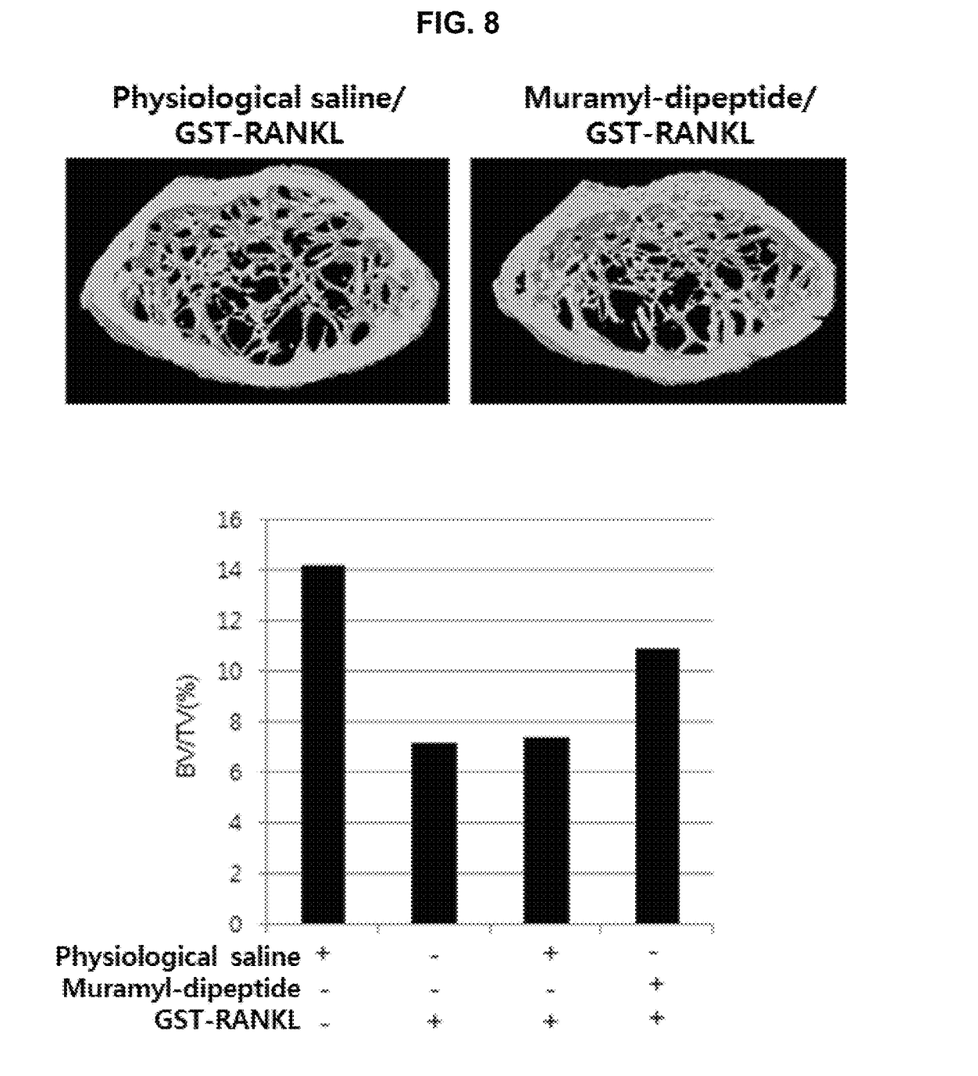
FIG. 8 is graphs showing the bone volume of the mouse model treated with the present muramyl-dipeptide prior to the administration of GST-RANKL that is known to induce bone loss to assess the effect of the present muramyl-dipeptide on the bone loss.

As shown in FIG. 8, when the mice were pretreated with muramyl dipeptide, the bone loss due to GST-RANKL was reduced compared to the controls in which the mice was not pretreated with muramyl dipeptide before the GST-RNAKL administration.

These results indicate the effect of muramyl dipeptide on the prevention of bone loss.

While the present invention has been shown and described in terms of various aspects, it will be apparent to those skilled in the art that various modification and changes may be made without departing the principles and spirit of the invention. Thus the scope of the invention must be defined by the appended claims and their equivalents.

With respect to the use of substantially any plural and/or singular terms herein, those having skill in the art can translate from the plural to the singular and/or form the singular to the plural as is appropriate to the context and/or application. The various singular/plural permutations may be expressly set forth herein for sake of clarity.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

What is claimed is:

1. A method of improving or treating a bone disorder in a subject in need thereof by reducing bone loss or promoting bone regeneration or formation, the method comprising administering to the subject a composition consisting of an effective amount of a muramyl-dipeptide or a muramyl-dipeptide derivative selected from the group consisting of N-acetylmuramyl-L-alanine-D-isoglutamine-lysine, 6-O-stearoyl-N-acetylmuramyl-L-alanine-D-isoglutamine, acetylglucosamine-N-acetylmuramyl-L-alanine-D-isoglutamine and acetylglucosamine-N-acetylmuramyl-L-alanine-D-isoglutamine-lysine, or a pharmaceutically acceptable salt thereof, wherein the bone disorder are osteoporosis, bone damage caused by bone metastasis of cancer cells, osteomalacia, rickets, adynamic bone disease, metabolic bone disease, osteolysis, bone deformity, osteoarthritis, deformity correction, dental correction, bone fracture treatment, osteosynthesis, bone regeneration of false joints, bone formation, and bone grafting.

2. The method of claim 1, wherein the muramyl-dipeptide is N-acetylmuramyl-L-alanyl-D-isoglutamine, N-acetylmuramyl-L-alpha-aminobutyryl-D-isoglutamine, N-acetylmuramyl-L-valyl-D-isoglutamine, or N-acetylmuramyl-L-seryl-D-isoglutamine.

3. The method of claim 1, wherein the composition is a pharmaceutical composition, a health food supplement, or a health functional food or a food additive.

4. The method of claim 1, wherein the osteoporosis is primary osteoporosis or secondary osteoporosis.

* * * * *